(12) United States Patent
Kuribara

(10) Patent No.: US 6,445,197 B1
(45) Date of Patent: Sep. 3, 2002

(54) ELECTRON BEAM TESTER, RECORDING MEDIUM THEREFOR AND SIGNAL DATA DETECTING METHOD

(75) Inventor: Masayuki Kuribara, Tokyo (JP)

(73) Assignee: Advantest Corporation, Tokyo (JP)

( * ) Notice: Subject to any disclaimer, the term of this patent is extended or adjusted under 35 U.S.C. 154(b) by 0 days.

(21) Appl. No.: 09/572,593

(22) Filed: May 17, 2000

(30) Foreign Application Priority Data

May 17, 1999 (JP) .............................................. 11-136214

(51) Int. Cl.$^7$ ............................................. G01R 31/305
(52) U.S. Cl. ........................ 324/751; 250/310; 250/311
(58) Field of Search ................................ 324/750, 751, 324/752, 71.3, 765, 158.1; 250/310, 311

(56) References Cited

U.S. PATENT DOCUMENTS 5,416,426 A  *  5/1995 Okubo et al. ................ 324/751

* cited by examiner

*Primary Examiner*—Michael Sherry
*Assistant Examiner*—Paresh Patel
(74) *Attorney, Agent, or Firm*—Rosenthal & Osha L.L.P.

(57) ABSTRACT

An electron beam tester, recording medium and a signal data detecting method capable of detecting whether or not the signal at a predetermined position of an electric component contains a jitter. The electron beam tester includes: a drive circuit which supplies a signal to the electric component; an electron gun which causes to emanate a secondary electron from the electric component by irradiating the electron beam to the electric component; a detector which detects an amount of the secondary electron emanated from the electric component; a first variation detecting unit which detects first variation data indicative of a magnitude of a variation amount of the secondary electron, with a voltage of the secondary electron being constant; a second variation detecting unit which detects second variation data, with a voltage fluctuation of the signal being indeterminate; and a voltage fluctuating data detecting unit which detects voltage fluctuating data indicative of a magnitude of voltage fluctuation when the voltage fluctuation of the signal is indeterminate.

15 Claims, 9 Drawing Sheets

VOLTAGE [V]

TIME [s]

Fig. 4B

SECONDARY ELECTRON CURRENT

SLICE LEVEL
ANALYSIS VOLTAGE [V]

Fig. 9A
VOLTAGE[V]
TIME[s]

Fig. 9B
VARIATION
VOLTAGE[V]
K
TIME[s]

Fig. 9C
VOLTAGE[V]
J
TIME[s]

ELECTRON BEAM TESTER, RECORDING MEDIUM THEREFOR AND SIGNAL DATA DETECTING METHOD

This patent application claims priority based on a Japanese patent application, H11-136214 filed on May 17, 1999, the contents of which are incorporated herein by reference.

BACKGROUND OF THE INVENTION

1. Field of the Invention

The present invention relates to an electron beam tester, recording medium thereof and a signal data detecting method. More particularly, the present invention relates to the electron beam tester for testing an electric component, the recording medium which stores a program executed by the electron beam tester and the signal data detecting method of detecting data on a signal at a predetermined position of the electric component.

2. Description of the Related Art

In the conventional practice, for example, an electron beam tester is used for testing electric components such as a semiconductor memory and so on. The electron beam tester irradiates an electron beam to an electric component to be tested. Then, by detecting a secondary electron amount generated at the electric component, an electron image of a strobe image of the electric component and a voltage waveform at a predetermined position of the electric component are obtained.

Figure 1A:
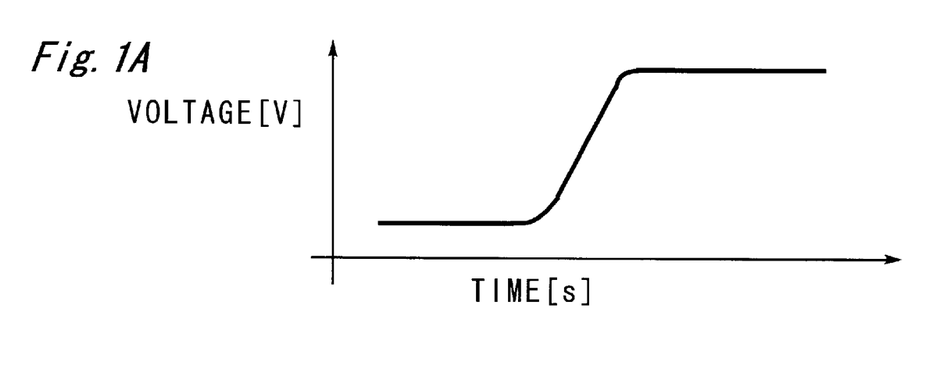
FIGS. 1A, 1B and 1C are provided in order to explain a voltage waveform, obtained by the electron beam tester, at a predetermined position of the electric component.
Figure 1B:
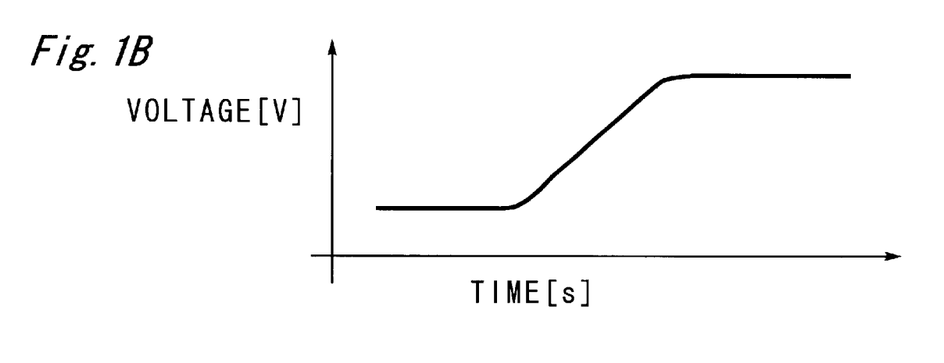
Figure 1C:
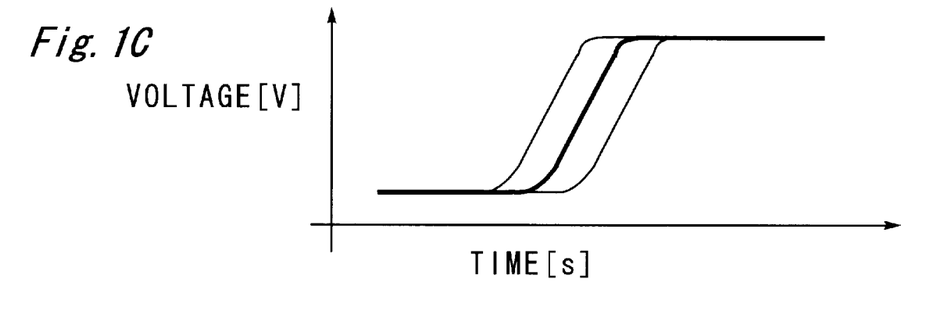

FIGS. 1A, 1B and 1C are provided in order to explain a voltage waveform, obtained by the electron beam tester, at a predetermined position of the electric component. When a signal shown in FIG. 1A is supplied to a predetermined position of the electric component, a voltage waveform shown in FIG. 1A is supposed to be obtained by the electron beam tester. However, there are occasions where a voltage waveform which is unwantedly deformed with respect to the voltage waveform shown in FIG. 1A is obtained instead of the ideal voltage waveform shown in FIG. 1A. Reasons why such a deformed voltage waveform is obtained are considered to be those as shown in FIG. 1C when a signal given contains a signal whose period is displaced, that is, the given signal contains a jitter, or that a signal per se in the electric component is deformed.

However, in the conventional electron beam tester, a problem occurs where a tester cannot distinguish which one of the following actually causes the deformation of the voltage waveform. Namely, such possible two causal factors are:

(1) a signal given contains a jitter, or (2) a signal per se in the electric component is deformed.

Moreover, recent years required are acquisition and detection of data on the signal at the electric component, such as the data on a voltage fluctuating amount of the signal and data on the phase of jitter in the case with the jitter being contained.

SUMMARY OF THE INVENTION

Therefore, it is an object of the present invention to provide an electron beam tester, recording medium and a signal data detecting method which overcome the above issues in the related art. This object is achieved by combinations described in the independent claims. The dependent claims define further advantageous and exemplary combinations of the present invention.

According to an aspect of the present invention, there is provided an electron beam tester for testing an electric component, the tester comprising: a drive circuit which supplies a signal to the electric component; an electron gun which causes to emanate a secondary electron from the electric component by irradiating the electron beam to a predetermined position of the electric component; a detector which detects an amount of the secondary electron emanated from the electric component; a first variation detecting unit which detects first variation data indicative of a magnitude of a variation amount of the secondary electron, based on the amount of the secondary electron detected by said detector at a predetermined position of the electric component, with a voltage of the secondary electron being constant; a second variation detecting unit which detects second variation data indicative of a magnitude of a variation amount of the secondary electron, based on the amount of the secondary electron detected by said detector at a predetermined position of the electric component, with a voltage fluctuation of the signal being indeterminate; and a voltage fluctuating data detecting unit which detects voltage fluctuating data indicative of a magnitude of voltage fluctuation when the voltage fluctuation of the signal is indeterminate.

In the electron beam tester where the drive circuit supplies to the electron component the signal having a predetermined period, and the voltage fluctuation of the signal is generated by a jitter in which the signal is displaced from the period, the electron beam tester may further comprise: an electron gun control unit comprising a first electron gun control section which instructs said electron gun to irradiate the electron beam synchronized with the first phase in which a voltage of the signal at the predetermined position stays fixed without being affected by the jitter; and a second electron gun control section which instructs said electron gun to irradiate the electron beam synchronized with a second phase in which a voltage of the signal at the predetermined position of the electric component fluctuates due to the jitter.

The first variation detecting unit detects a first variation data indicative of a magnitude of the secondary electron amount, based on the secondary electron amount detected by said detector as a result of the electron beam irradiated from the said electron gun by said first electron gun control section.

The second variation detecting unit detects a second variation data indicative of a magnitude of the secondary electron amount, based on the secondary electron amount detected by said detector as a result of the electron beam irradiated from said electron gun by said second electron gun control section.

The voltage fluctuating data detecting unit detects a magnitude of the voltage at the second phase due to the jitter, based on the first variation data and the second variation data.

The electron beam tester may further comprise: a driver which outputs a desired analysis voltage which serves to control the degree of the secondary electron taken in for detection, in a varying manner, said detector detecting the secondary electron taken in by the analysis voltage; a coincidence analysis voltage detecting unit which detects a coincidence analysis voltage that coincides with a reference secondary electron amount or a slice level set in advance; and a phase determining unit which determines the first phase and the second phase based on the coincidence analysis voltage.

The electron beam tester may further comprise: a driver output control unit which instructs the driver to output a same analysis voltage as the coincidence analysis voltage, at the first phase, detected by the coincidence analysis voltage detecting unit when the electron beam is irradiated from the electron gun by the first electron gun control unit, and which instructs the driver to output a same analysis voltage as the coincidence analysis voltage, at the second phase, detected by the coincidence analysis voltage detecting unit when the electron beam is irradiated from the electron gun by the second electron gun control section.

Moreover, the voltage fluctuating data detecting unit may detect the voltage fluctuating data by subtracting the first variation data from the second variation data.

Moreover, a plurality of phases may be used as the second phase.

The electron beam tester may further comprise a voltage fluctuating amount detecting unit which detects a voltage fluctuating amount due to the jitter at the second phase, based on the voltage fluctuating data.

Moreover, the voltage fluctuating amount detecting unit may detect the voltage fluctuating amount based on relationship between the analysis voltage at the second phase and the secondary electron amount detected by the detector.

The electron beam tester may further comprise a display unit which displays relationship between the voltage fluctuating amount and the second phase of the signal.

The electron beam tester may further comprise: a phase data detecting unit which detects phase data indicating a phase of the jitter, based on the voltage fluctuating amount; and a display unit which displays the phase data on the jitter.

The electron beam tester may further comprise a phase voltage detecting unit which detects a voltage of the signal at the phase at a predetermined position of the electric component, based on the coincidence analysis voltage detected by the coincidence analysis voltage detecting unit.

Moreover, the phase voltage detecting unit detects the phase data indicating a phase of the jitter, based on a voltage of the signal at the phase detected by the phase voltage detecting unit and the voltage fluctuating amount.

Moreover, the phase data detecting unit may detect the phase data indicating a phase of the jitter, based on the wave form obtained by adding to voltages of the signal at a plurality of phases detected by the phase voltage detecting unit the voltage fluctuating amount at the phase in question.

Moreover, the phase data detecting unit detects the phase data indicating a phase of the jitter, based on reference voltage change data which represent a relationship between a phase and a voltage fluctuation of a jitter-free reference signal, and the voltage fluctuating amount.

According to another aspect of the present invention there is provided a recoding medium storing an executable program in an electron beam tester comprising a drive circuit for supplying a signal to an electric component, an electron gun for causing to emanate a secondary electron from the electric component by irradiating an electron beam to a predetermined position of the electric component, and a detector for detecting an amount of the secondary electron emanated from the electric component, in which the program comprises: a first program which instructs to detect first variation data indicative of a magnitude of variation of the secondary electron amount, based on the secondary electron amount detected by the detector while a voltage of the signal stays fixed at the predetermined position of the electric component; a second program which instructs to detect second variation data indicative of a magnitude of variation of the secondary electron amount, based on the secondary electron amount detected by the detector while a voltage fluctuation of the signal is indeterminate at the predetermined position of the electric component; and a third program which instructs to detect voltage fluctuating data indicating a fluctuating magnitude of a voltage in the case of a voltage fluctuation of the signal being indeterminate, based on the first variation data and the second variation data.

According to still another aspect of the present invention, there is provided a method of detecting data on a signal at a predetermined position of an electric component when testing the electric components, the signal data detecting method comprising: (1) causing to emanate a secondary electron from the electric component by irradiating an electron beam to the predetermined position of the electric component; (2) detecting the secondary electron; (3) detecting first variation data indicative of a magnitude of the secondary electron, based on an amount of the secondary electron detected in said detecting the secondary electron in a case where a voltage of the signal at the predetermined position of the electric component stays fixed; (4) detecting second variation data indicative of a magnitude of the secondary electron, based on an amount of the secondary electron detected in said detecting the secondary electron in a case where a voltage fluctuation of the signal at the predetermined position of the electric component is indeterminate; (5) detecting voltage fluctuating data indicative of the voltage fluctuation in the case of the voltage of the signal being indeterminate thus containing a jitter, based on the first variation data and the second variation data.

This summary of the invention does not necessarily describe all necessary features of the present invention. The present invention may also be a sub-combination of the above-described features. The above and other features and advantages of the present invention will become more apparent from the following description of embodiments taken in conjunction with the accompanying drawings.

The invention will now be described based on the preferred embodiments, which do not intend to limit the scope of the present invention, but exemplify the invention. All of the features and the combinations thereof described in the embodiment are not necessarily essential to the invention.

Figure 2:
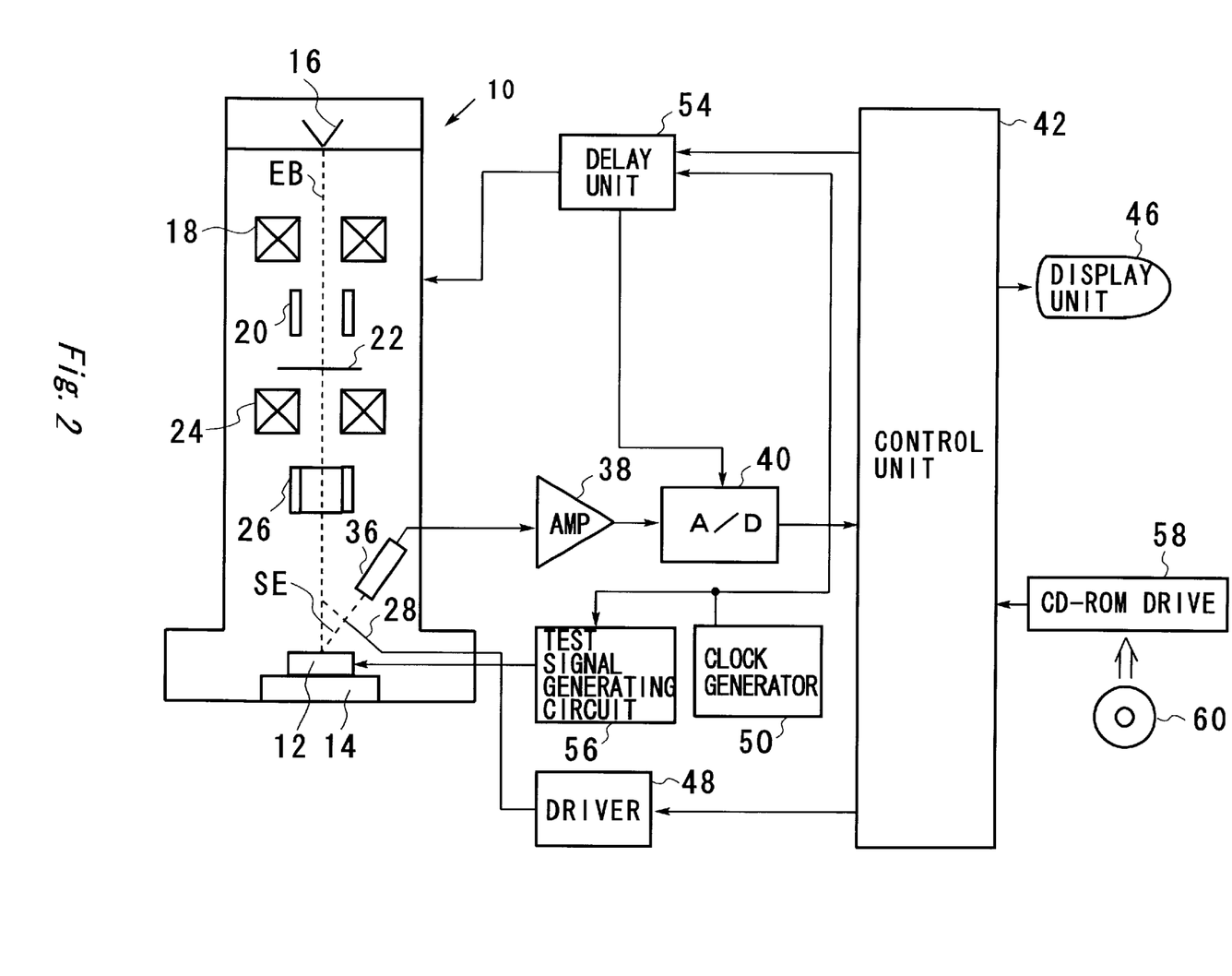
FIG. 2 shows a configuration of an electron beam tester according to an embodiment of the present invention.

FIG. 2 shows a configuration of an electron beam tester according to an embodiment of the present invention. In the interior of an electron beam barrel 10 of the electron beam tester, an electron beam EB is irradiated from an electron gun 16. The electron beam EB irradiated from the electron gun 16 is irradiated to a predetermined position of an electric component 12 placed on a stage 14, through a first magnetic lens 18, a polarizing plate, a chopping aperture 22, a second magnetic lens 24 and a deflector 26. Secondary electrons SE generated by irradiating the electron beam EB to the electric component 12 are detected by a detector 36 via an energy filter 28. A predetermined analysis voltage is applied to the energy filter 28 by a driver 48.

The detector 36 inputs an amount of the secondary electrons detected (secondary electron amount) to an amplifier 38. The secondary electron amount which is input to the amplifier 38 is amplified and then is converted to a digital signal by an analog-to-digital converter 40 (referred to as an A-D converter 40 hereafter). Thereafter, the A-D converted digital signal is input to a control unit 42. The control unit controls the driver 48 and a delay unit 54 based on the input secondary electron amount. Moreover, the control unit 42 outputs a processed result to a display unit 46. A CD-ROM drive 58 which reads out data from a CD-ROM (as an exemplary recording medium) is connected to the control unit 42.

A clock generator 50 generates a predetermined clock signal which is then supplied to a test signal generating circuit 56 and the delay unit 54 which serve as drive circuits. The test signal generating circuit 56 sends the electric component 12 a signal based on the clock signal supplied. In the present embodiment, the test signal generating circuit 54 sends a periodic signal to the electric component 12. The delay unit controls each element inside the electron beam barrel 10, based on the supplied clock signal. For example, the delay unit 54 irradiates the electron beam by the electron gun 16, based on the supplied clock signal.

Figure 3:
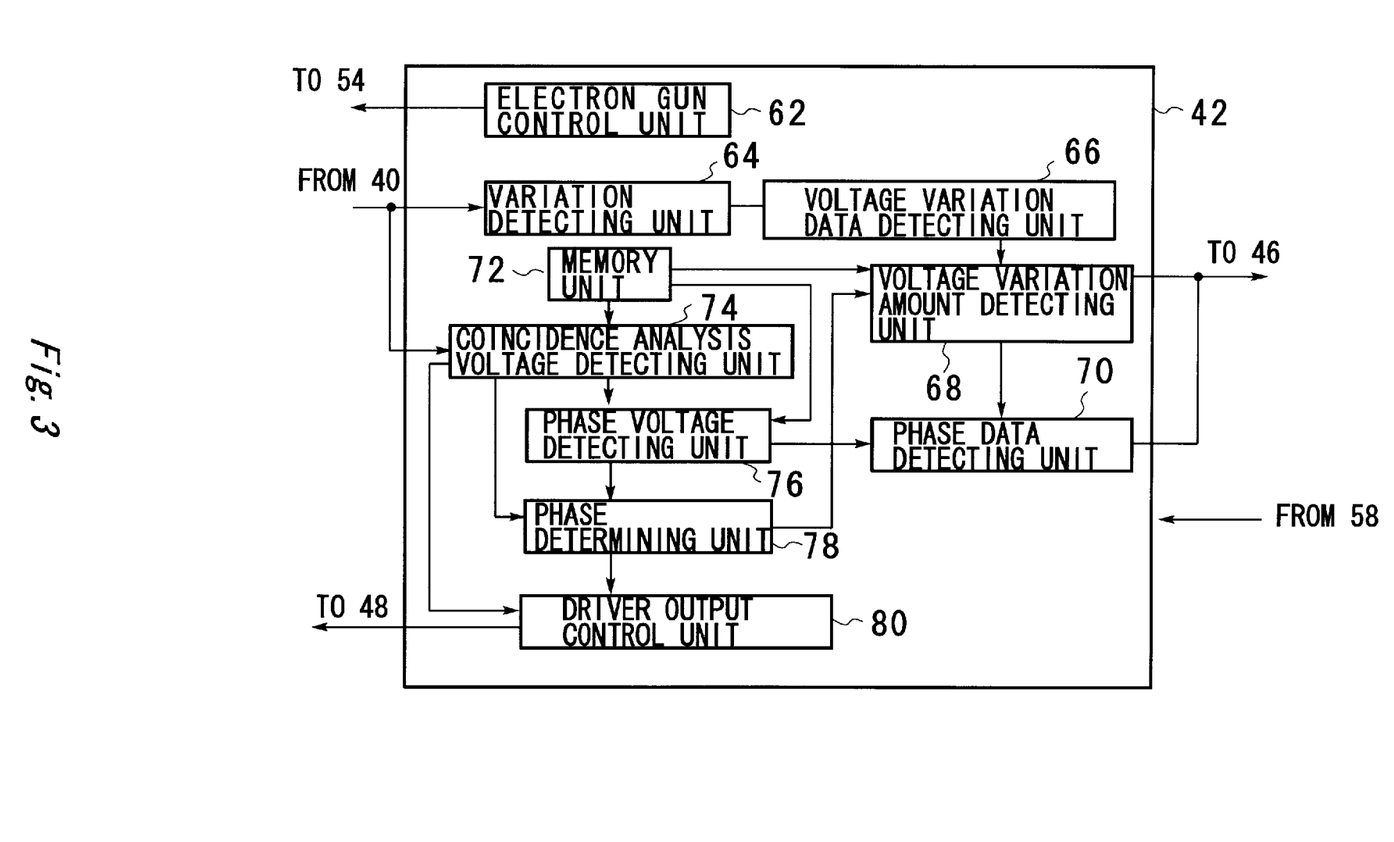
FIG. 3 shows a detailed structure of the control unit according to an embodiment of the present invention.

FIG. 3 shows a detailed structure of the control unit according to an embodiment of the present invention. The control unit 42 comprises: an electron gun control unit 62 exemplified by a first electron gun control section and a second electron gun control section; a variation detecting unit 64 exemplifying a first variation detecting unit; a voltage variation data detecting unit 66 exemplifying a second variation detecting unit; a voltage variation amount detecting unit 68; a phase data detecting unit 70; a memory unit 72; a coincidence analysis voltage detecting unit 74; a phase voltage detecting unit 76; a phase determining unit 78; and a driver output control unit 80. Functions of the above respective units will be described at a later stage. These units 62–80 may be provided as software modules by the CD-ROM 60. In that case, the control unit 42 reads out a program of the software module from the CD-ROM 60 by the CD-ROM driver 58.

Figure 4A:
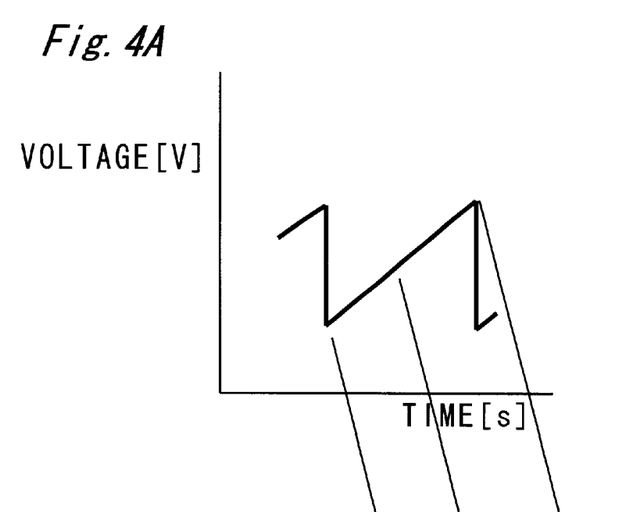
FIGS. 4A and 4B serve to explain the relationship between a voltage waveform of the electric component 12 at a predetermined position and the secondary electron amount detected by the detector 36.
Figure 4B:
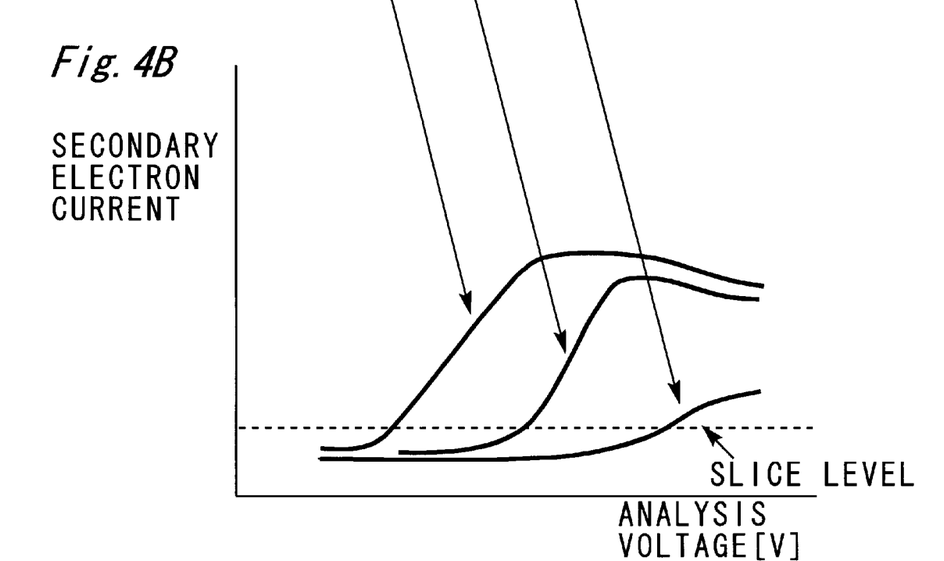

FIGS. 4A and 4B serve to explain the relationship between a voltage waveform of the electric component 12 at a predetermined position and the secondary electron amount detected by the detector 36 at that position. FIG. 4A shows the voltage waveform of the electric component 12 in a predetermined position. FIG. 4B shows the relationship between the secondary electron amount and an analysis voltage when the electric component 12 at the predetermined position presents the predetermined voltage shown in FIG. 4A.

Referring to FIG. 4B, the relationship between the secondary electron amount detected by the detector 36 and the analysis voltage is represented by an S-shaped graph (a so-called S curve) even when the voltage of the electric component 12 in the predetermined position differs. Namely, in a range where the analysis voltage is relatively low, the secondary electron amount barely increases even when the analysis voltage increases. In another range where the analysis voltage is slightly higher, the secondary electron amount increases at almost a constant rate as the analysis voltage increases. In a range where the analysis voltage is relatively high, the secondary electron amount barely increases and almost stays stable.

This S curve as an entire graph is displaced toward the direction of the higher analysis voltage, as a potential of the electric component in the predetermined position is high. observing the S curve, in the range where the secondary electron amount increases at almost a constant rate as the analysis voltage increases, the secondary electron amount detected by the detector 36 is proportional to the difference between the voltage of the signal of the electric component 12 and the analysis voltage. Thus, the voltage of the signal of the electric component 12 can be calculated from the analysis voltage. In the electron beam tester, the secondary electron amount belonging in the range where the secondary electron amount changes at a constant rate in all of a plurality of S curves for each voltage at the predetermined position of the electric component 12 is generally taken as a reference secondary electron amount (slice level), so that the analysis voltage at the slice level is detected and then a voltage of the electric component 12 is calculated based on the analysis voltage.

The memory unit 72 stores data on the slice level, a corresponding relationship between the analysis voltage and the voltage of the electric component at the slice level, and another corresponding relationship (S curves) between the secondary electron amount at a plurality of voltages in the electric component and the analysis voltage.

Next, operation of the electron beam tester according to an embodiment of the present invention will be described.

First, synchronized with a predetermined phase at a predetermined position of the electric component 12, the electron gun 62 irradiates the electron beam to the electric component 12. Next, a driver output control unit 80 gradually varies the analysis voltage output from the driver 48. At the same time, the coincidence analysis voltage detecting unit 74 detects an analysis voltage (a coincidence analysis voltage) in which the secondary electron amount detected by the detector 36 with respect to the phase at the predetermined position of the electric component 12 coincides with the slice level stored in the memory unit 72.

Next, based on the relationship between the analysis voltage and the voltage of the electric component 12 in the slice level stored in the memory unit 72, the phase voltage detecting unit 76 detects a voltage value corresponding to the analysis voltage in the phase. Then, the above operation is performed on a plurality of phases at the predetermined position of the electric component. Thereby, the coincidence analysis voltage and voltage value can be detected at a plurality of the phases in the predetermined position of the electric component.

Next, based on the coincidence analysis voltage at a plurality of the phases in the predetermined positions of the electric component, the phase determining unit 78 determines a firs phase where the voltage at the electric component 12 is constant irrespective of jitter and a second phase where the voltage at the electric component fluctuates due to jitter.

Figure 5:
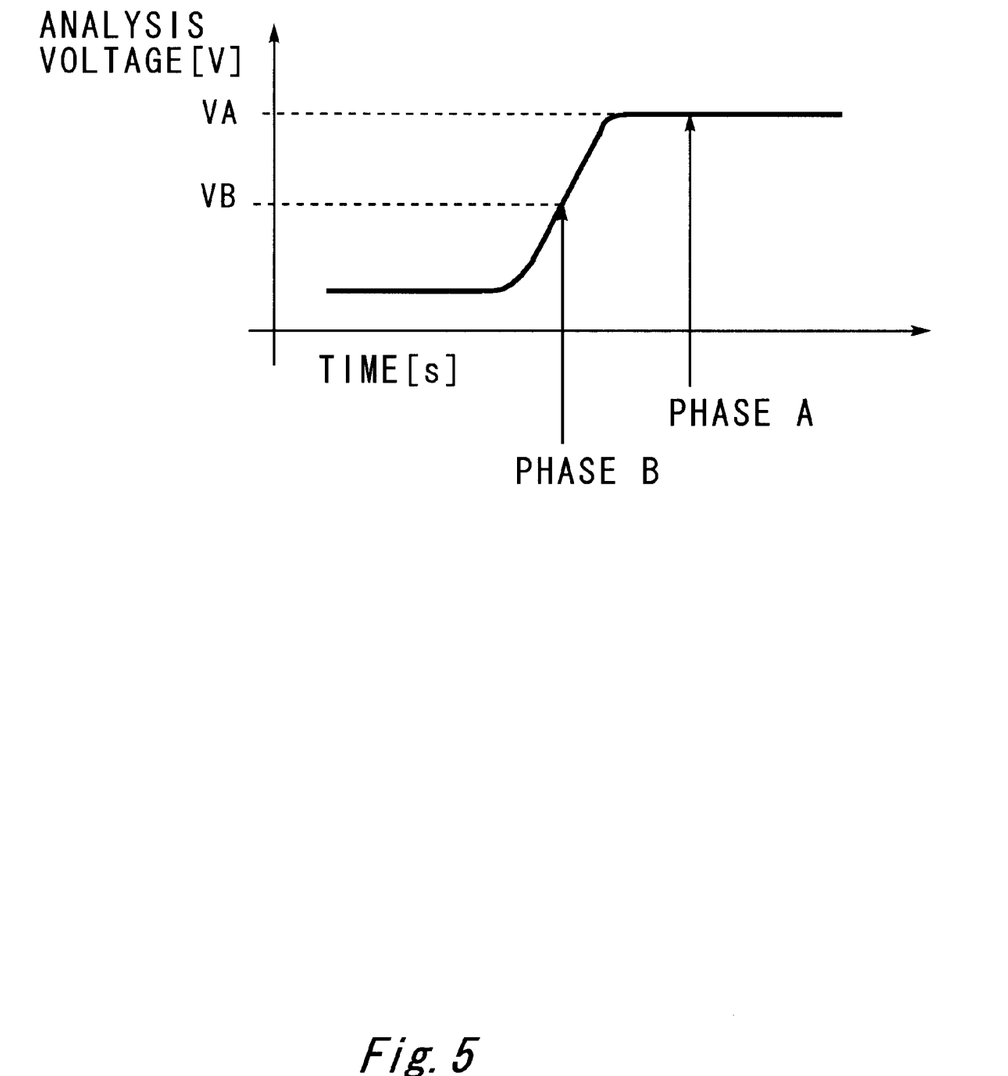
FIG. 5 explains a phase determined by the phase determining unit 78 according to an embodiment of the present invention.

FIG. 5 explains a phase determined by the phase determining unit 78 according to an embodiment of the present invention. In FIG. 5, the horizontal axis represents time while the vertical axis represents the coincidence analysis voltage.

The phase determining unit 78 according to the present embodiment determines a phase A, as the first phase, which belongs to a range where the coincidence analysis voltage progresses at the same level, that is, the voltage at the electric component 12 stays at a constant level. Here, let us denote the coincidence analysis voltage at the phase A, by $V_A$. Moreover, the phase determining unit 78 determines a phase B, as the second phase, which belongs to a range where the coincidence analysis voltage changes. Here, let us denote the coincidence analysis voltage at the phase B, by $V_B$. In the present embodiment, the phase determining unit 78 determines a plurality of positions as the second phase.

Next, the electron gun control unit 62 instructs the delay unit 54 so that the electron beam which is synchronized with the first phase such as the phase A is irradiated to the electric component 12.

Next, synchronized with the first phase such as the phase A which is determined by the phase determining unit 78, the electron beam is irradiated to the electric component 12b the delay unit 54. At the same time, the driver output control unit 80 outputs to the driver 48 the coincidence analysis voltage at the first phase (e.g. the coincidence analysis voltage $V_A$ in the case of the phase A). Then, the detector 36 detects the secondary electron amount and outputs it to the variation detecting unit 64 via the amplifier 38 and the A-D converter 40.

Thereafter, the operation in which the secondary electron amount is detected by irradiating the electron beam synchronized with the first phase, is performed a plural number of times. Next, based on the plural secondary electron amounts detected by the detector 36, the variation detecting unit 64 detects the first variation data indicating the variation of the secondary electron amount such as a distributed value (first distributed value). The variation of the secondary electron amount at the first phase is due mainly to the process itself of detecting the secondary electron amount by irradiating the electron beam.

Next, synchronized with the second phase determined by the phase determining unit 78 such as the phase B, the electron gun control unit 62 irradiates the electron beam to the electric component 12 by the delay unit 54. At the same time, the driver output control unit 80 outputs to the driver 48 the coincidence analysis voltage at the second phase (e.g. the coincidence analysis voltage $V_B$ in the case of the phase B). Then, the detector 36 detects the secondary electron amount and outputs it to the variation detecting unit 64 via the amplifier 38 and the A-D converter 40. Thereafter, the operation in which the secondary electron amount is detected by irradiating the electron beam while synchronized with the second phase, is performed a plural number of times. In the present embodiment, the operation in which the secondary electron amount is detected with respect to the plural phases as the second phase is performed.

The variation of the second electron amount at the second phase is primarily caused by the process itself of detecting the secondary electron amount by irradiating the electron beam, and a voltage fluctuation of a signal at the electric component 12 (e.g. jitter). Next, based on a plurality of the secondary amounts at each phase the variation detection unit 64 detects by the detector 36, the second variation data such as a distributed value (the second distributed value) indicating the magnitude of the secondary electron amount at each phase is detected.

Next, based on the first variation data and the second variation data, the voltage variation data detecting unit 66 detects the voltage fluctuation data indicating the magnitude of the voltage fluctuation in the second phase. In the present embodiment, the voltage variation data detecting unit 66 detects the voltage fluctuation data indicating the magnitude of the voltage variation in such a manner that the first distributed value is subtracted from the second distributed value. Here, as described above, the variation of the secondary electron amount at the second phase is caused mainly by the process itself of detecting the secondary electron amount by irradiating the electron beam, and the voltage change in the signal at the electric component 12. The variation of the secondary electron amount at the first phase is caused mainly by the processing itself of detecting the secondary electron amount by irradiating the electron beam.

Thereby, the value obtained by subtracting the first distributed value from the second distributed value is the distributed value of the secondary electron amount, due to the voltage variation of the signal at the electric component in the second phase or a value strongly associated with it. Let us denote this value by a third distributed value. In the present embodiment, the voltage variation data detecting unit 66 detects the voltage variation data about the second phase at a plurality of phases. In this specification, the terms variation and fluctuation are used interchangeably.

Next, based on the voltage variation data detected by the voltage variation data detecting unit 66 at the second phase, the voltage variation amount detecting unit 68 calculates the voltage variation amount at the second phase. In the present embodiment, the voltage variation amount detecting unit 68 calculates a square root of the third distributed value which is detected by the voltage variation data detecting unit 66 at the second phase. Here, the third distributed value is a distributed value of the secondary electron amount caused by the voltage fluctuation of the signal at the electric component 12 at the second phase, or a value strongly associated with it. Thus, the square root of the third distributed value will be a standard deviation of the secondary electron amount due to the voltage variation of the signal at the electric component 12 at the second phase, or will be a value close to it.

Figure 6:
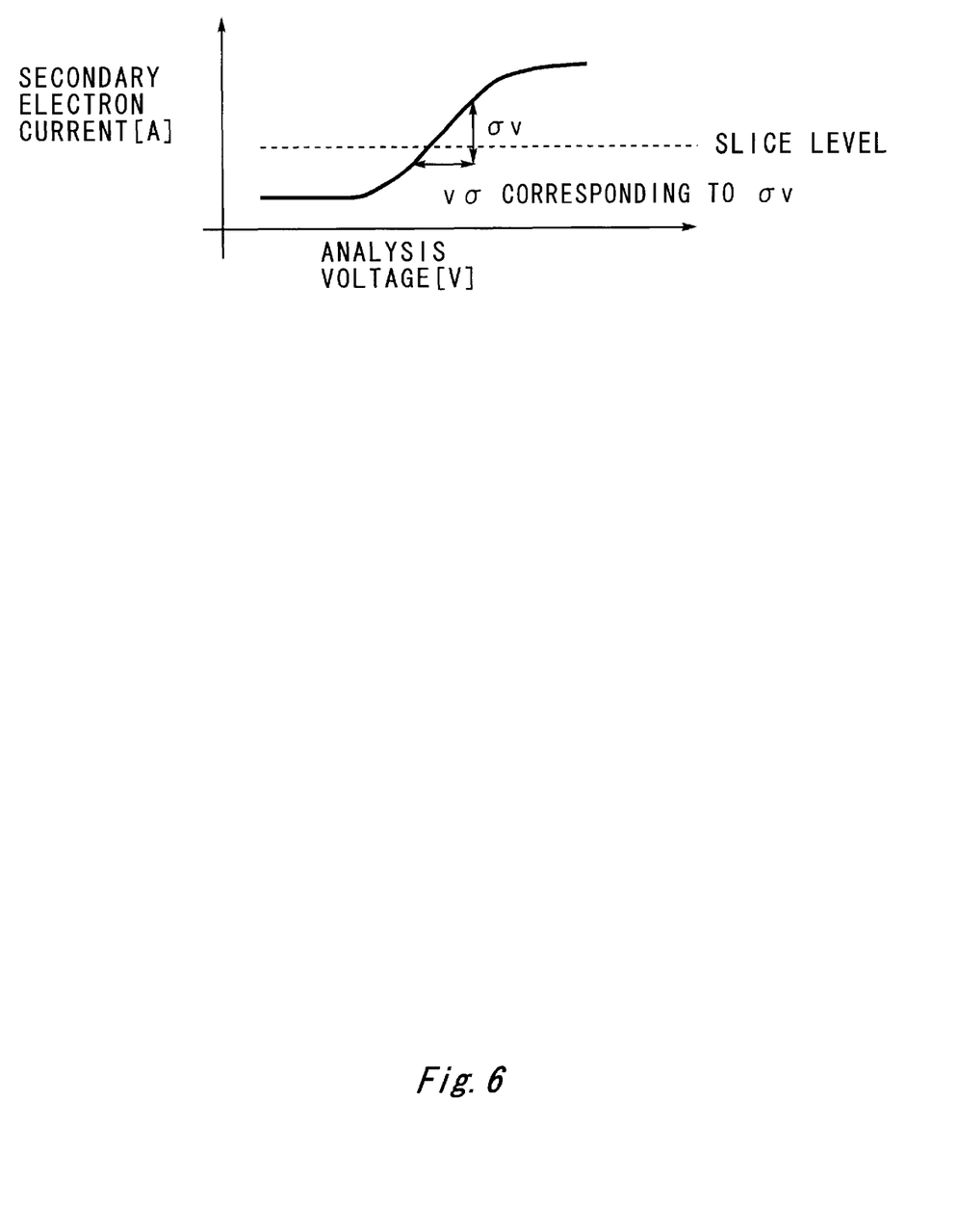
FIG. 6 illustrates a process of obtaining the voltage variation by the voltage variation amount detecting unit 68 according to the present embodiment.

FIG. 6 illustrates a process of obtaining the voltage variation by the voltage variation amount detecting unit 68 according to the present embodiment. After the voltage variation amount detecting unit 68 calculates the square root of the third distributed value at the second phase, the S curve at the second phase shown in FIG. 6 is read out of the memory unit 72, so that an analysis voltage $V_O$ corresponding to the width of the secondary electron amount equivalent to the square root (that is $\sigma_V$ in FIG. 6) is detected and is converted to a voltage value at the electric component, based on the analysis voltage. Here, the range of the S curve used when detecting the analysis voltage corresponding to the square root, is preferably in the close vicinity of the slice level of the S curve.

The voltage variation amount detecting unit 68 instructs a display unit 46 to display data indicating a relationship between the second phase and voltage fluctuating amount detected, such as a graph showing this relationship. In the present embodiment, the voltage variation amount detecting unit 68 instructs the display unit 46 to display a graph showing the phase and the voltage fluctuating amount related to a plurality of phases as the second phase.

Figure 7:
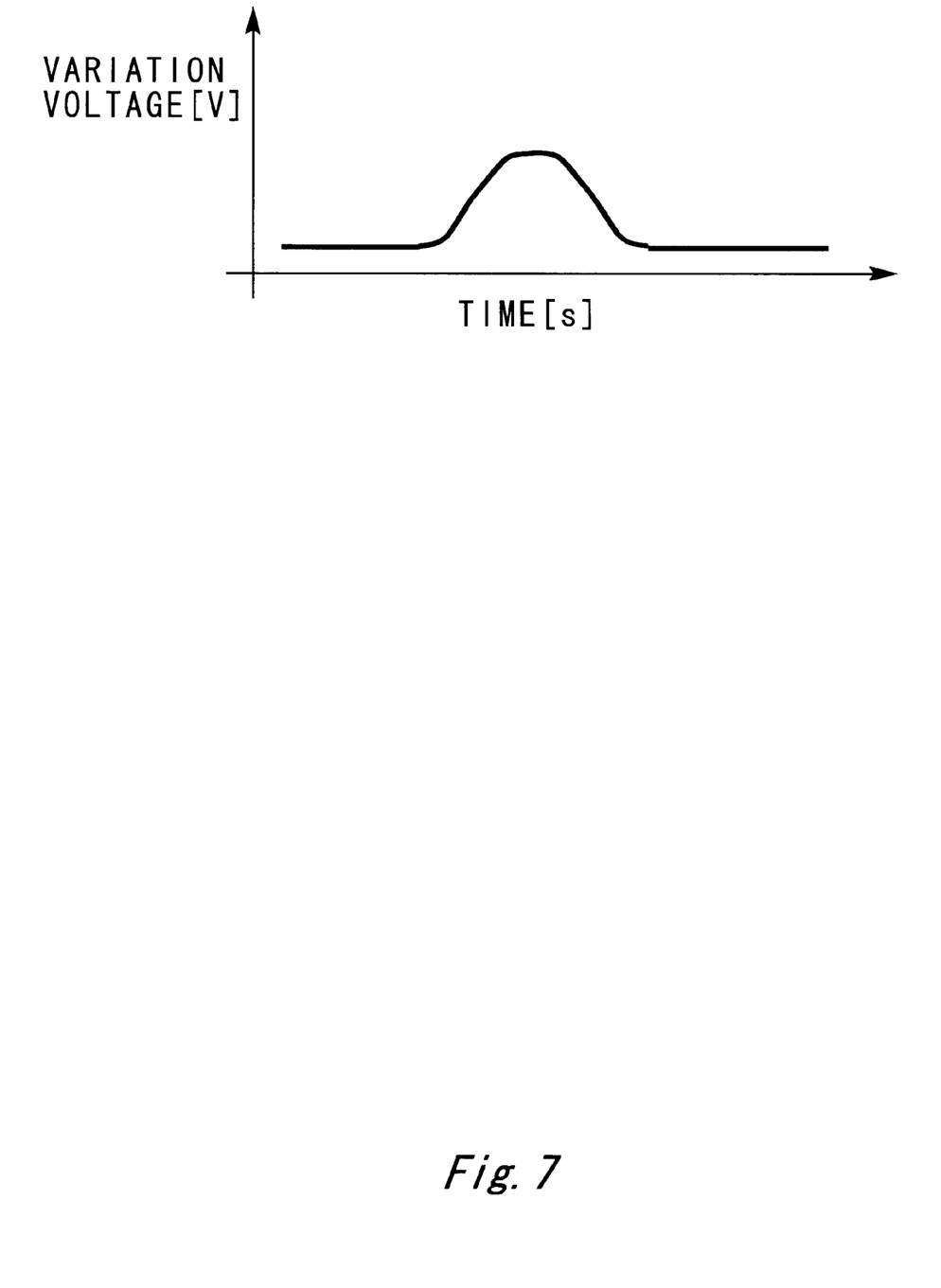
FIG. 7 is a graph showing an exemplary relationship between the second phase and the voltage fluctuating amount displayed in the display unit 46 according to an embodiment of the present invention.

FIG. 7 is a graph showing an exemplary relationship between the second phase and the voltage fluctuating amount displayed in the display unit 46, according to an embodiment of the present invention. The display unit 46 displays a graph in which the horizontal axis indicates the phase while the vertical axis indicates the voltage variation value at each phase.

The phase data detecting unit 70 detects the phase data indicating a phase of the jitter based on the voltage variation amount detected by the voltage variation amount detecting unit 68, and displays the phase data in the display unit 46.

Figure 8A:
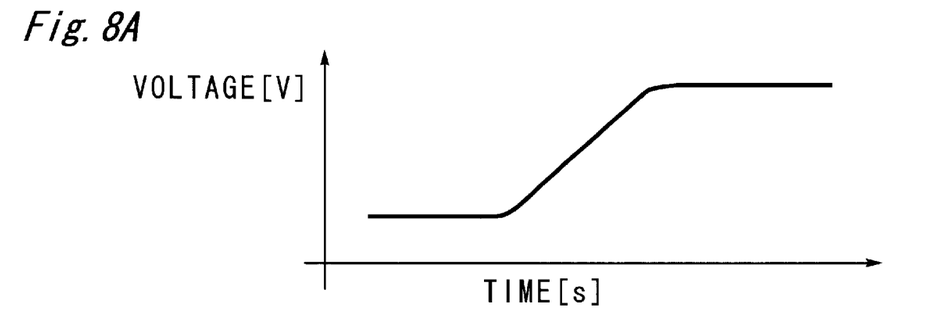
FIGS. 8A, 8B and 8C show an exemplary operation in which the phase data detecting unit 70 according to an embodiment of the present invention detects the phase data of the jitter.
Figure 8B:
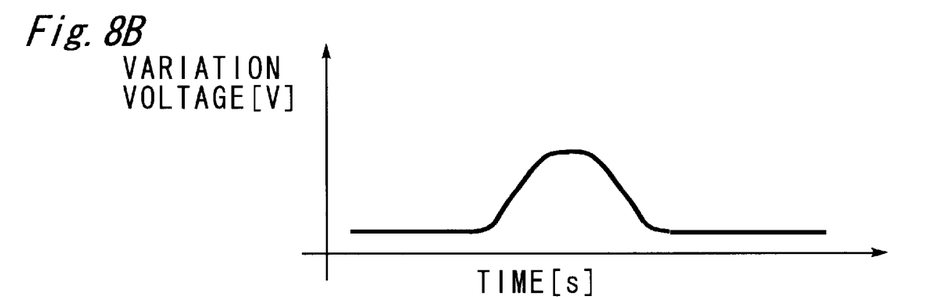

FIGS. 8A, 8B and 8C show an exemplary operation in which the phase data detecting unit 70 according to an embodiment of the present invention detects the phase data of the jitter. The phase data detecting unit 70 adds to or subtracts from the voltage value (shown in FIG. 8A) a teach phase at the predetermined position of the electric component 12 detected by the phase voltage detecting unit 76, the voltage variation amount (shown in FIG. 8B) detected by the voltage variation amount detecting unit 68 shown at each phase.

Figure 8C:
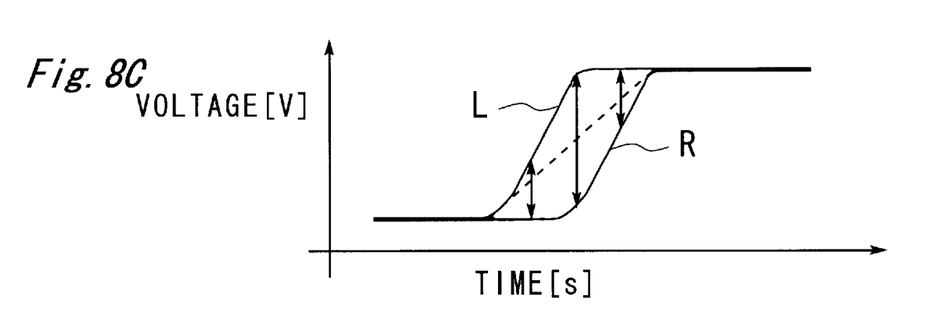

In the above manner, a voltage waveform of the signal containing the jitter (shown in FIG. 8C) is obtained. Next, a leftmost jitter waveform L and a rightmost jitter waveform R in the voltage waveform shown in FIG. 8C are detected, so that the width of the phase between the jitter waveform L and the jitter waveform R is detected. Then, the phase data detecting unit 70 instructs the display unit 46 to display data indicating the phase of the jitter, for example, the graph of the voltage waveform and the width of the detected phase shown in FIG. 8C. In this manner, according to the present embodiment, data on the phase of the jitter contained in the signal at the predetermined position of the electric component 12 can be detected.

Figure 9A:
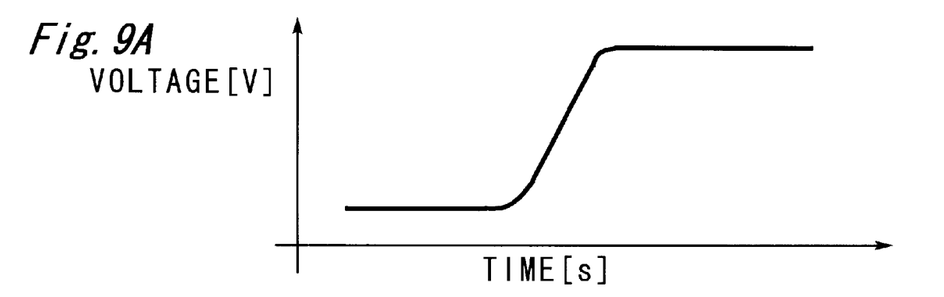
FIGS. 9A, 9B and 9C shows another exemplary operation in which the phase data detecting unit 70 detects the phase data of the jitter according to another embodiment of the present invention.
Figure 9B:
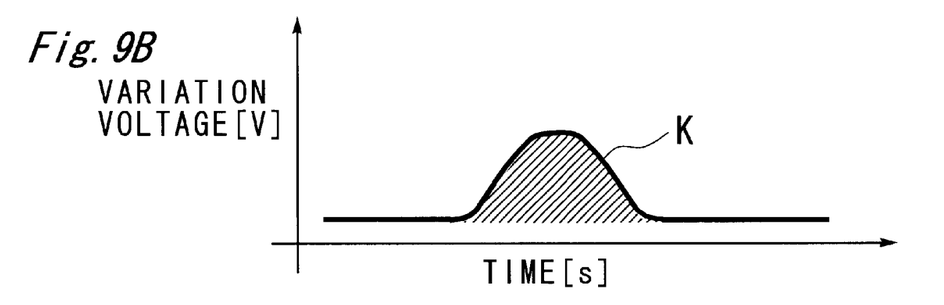
Figure 9C:
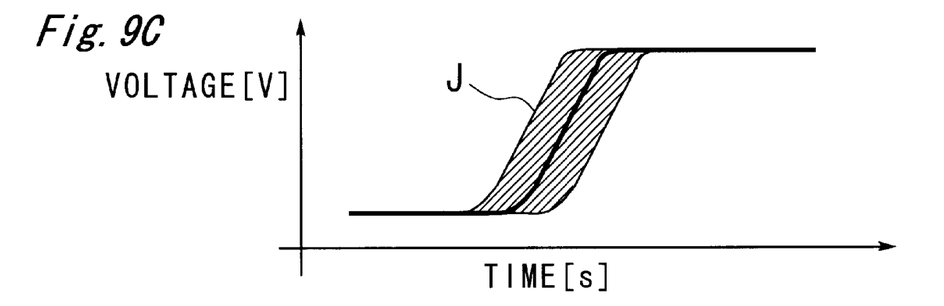

FIGS. 9A, 9B and 9C show another exemplary operation in which the phase data detecting unit 70 detects the phase data of the jitter according to the another embodiment of the present invention. Suppose that an ideal voltage waveform of the signal at the predetermined position of the electric component 12 shown in FIG. 9A is provided in advance in the memory unit 72. The phase data detecting unit 70 shifts the ideal signal shown in FIG. 9A, in the same time interval along the time axis as shown in FIG. 9C.

Then, the phase data detecting unit 70 adjusts a region J of FIG. 9C enclosed by the signals so that the region J can be twice as much as the voltage variation amount (a region denoted by K in FIG. 9B) which is obtained by voltage variation amount at each phase detected by the voltage variation amount detecting unit 68. The waveform of the signal shown in FIG. 9C in the case where the region J is equal to the region 2 times K, represents the voltage waveform of the signal containing the jitter at the predetermined position of the electric component 12. The phase data detecting unit 70 detects the time width (time interval) at the time when the signal is shifted at this time, that is, the time width (time interval) of the jitter. Then, for example, the phase data detecting unit 70 instructs the display unit 46 to display a graph shown in FIG. 9C in the case where the region J is equal to the region 2 times K, and the time width (time interval) if the jitter detected by the above processing.

In this manner, according to the present embodiment, data on the phase of the jitter contained in the signal at the predetermined position of the electric component 12 can be detected.

Now, the present invention is not limited by the above present embodiments, and various modifications are possible. For example, though the CD-ROM 60 is used as the recording medium in the above embodiment, any recording medium will serve as such which can store programs such as optical recording medium (a DVD (Digital Video Disk) and so on), optical magnetic recording medium (MO and so on), magnetic recording medium (a floppy disk and so on) and a semiconductor recording medium (IC card and the like).

Though the distributed value is used as data indicating the magnitude of the variation in the above embodiments, the present invention is not limited to it alone, and data may be anything that can indicate the magnitude of the fluctuation, for example, the standard deviation may serve the purpose.

As is apparent from the above description, according to the present invention, information on the voltage variation amount and the phase of jitter of the signal in the electric parts can be detected.

Although the present invention has been described by way of exemplary embodiments, it should be understood that many changes and substitutions may be made by those skilled in the art without departing from the spirit and the scope of the present invention which is defined only by the appended claims.

What is claimed is:

1. An electron beam tester for testing an electric component, comprising:

a drive circuit which supplies a signal to the electric component;

an electron gun which causes to emanate a secondary electron from the electric component by irradiating the electron beam to a predetermined position of the electric component;

a detector which measures an amount of the secondary electron emanated from the electric component and outputs a signal representing the amount of the secondary electron, the outputted signal comprising a first phase including a substantially constant voltage and a second phase which follows the first phase and includes a non-constant voltage;

a first variation detecting unit which calculates a signal outputted by the detector and outputs a first distributed value indicating fluctuation of a voltage of the outputted signal, the first variation detecting unit calculating out the first distributed value at a particular data of the outputted signal in the first phase;

a second variation detecting unit which calculates the outputted signal and the first distributed value, calculates out a second distributed value indicating fluctuation of a voltage of signal outputted by the detector, and outputs a third distributed value by subtracting the first distributed value from the second distributed value, the second variation detecting unit calculating out the second distributed value at a particular data of the outputted signal in the second phase; and a voltage variation amount detecting unit which outputs a voltage with a phase data corresponding to the third distributed value.

2. An electron beam tester of claim 1, in which said drive circuit supplies to the electric component the signal having a predetermined period, and the voltage fluctuation of the signal is generated by a jitter in which the signal is displaced from the period, the electron beam tester further comprising:
an electron gun control unit comprising a first electron gun control section and a second electron gun control section;
the first electron gun control section which instructs said electron gun to irradiate the electron beam synchronized with the first phase in which a voltage of the signal at the predetermined position stays fixed without being affected by the jitter; and
the second electron gun control section which instructs said electron gun to irradiate the electron beam synchronized with a second phase in which a voltage of the signal at the predetermined position of the electric component fluctuates due to the jitter;
wherein said first variation detecting unit detects a first variation data indicative of a magnitude of the secondary electron amount, based on the secondary electron amount detected by said detector as a result of the electron beam irradiated from the said electron gun by said first electron gun control section,
wherein said second variation detecting unit detects a second variation data indicative of a magnitude of the secondary electron amount, based on the secondary electron amount detected by said detector as a result of the electron beam irradiated from said electron gun by said second electron gun control section and
wherein said voltage fluctuating data detecting unit detects a magnitude of the voltage at the second phase due to the jitter, based on the first variation data and the second variation data.

3. An electron beam tester of claim 2, further comprising:
a driver which outputs a desired analysis voltage which serves to control the degree of the secondary electron taken in for detection, in a varying manner, said detector detecting the secondary electron taken in by an analysis voltage;
a coincidence analysis voltage detecting unit which detects a coincidence analysis voltage that coincides with a reference secondary electron amount set in advance; and
a phase determining unit which determines the first phase and the second phase based on the coincidence analysis voltage.

4. An electron beam tester of claim 3, further comprising:
a driver output control unit which instructs said driver to output a same analysis voltage as the coincidence analysis voltage, at the first phase, detected by said coincidence analysis voltage detecting unit when the electron beam is irradiated from the electron gun by the first electron gun control section, and which instructs said driver to output a same analysis voltage as the coincidence analysis voltage, at the second phase, detected by said coincidence analysis voltage detecting unit when the electron beam is irradiated from the electron gun by the second electron gun control section.

5. An electron beam tester of claim 2, wherein a plurality of phases are used as the second phase.

6. An electron beam tester of claim 2, further comprising a voltage fluctuating amount detecting unit which detects a voltage fluctuating amount due to the jitter at the second phase, based on the voltage fluctuating data.

7. An electron beam tester of claim 6, wherein said voltage fluctuating amount detecting unit detects the voltage fluctuating amount based on relationship between an analysis voltage at the second phase and the secondary electron amount detected by said detector.

8. An electron beam tester of claim 6, further comprising a display unit which displays relationship between the voltage fluctuating amount and the second phase of the signal.

9. An electron beam tester of claim 6, further comprising:
a phase data detecting unit which detects phase data indicating a phase of the jitter, based on the voltage fluctuating amount; and
a display unit which displays the phase data on the jitter.

10. An electron beam tester of claim 9, further comprising a phase voltage detecting unit which detects a voltage of the signal at the phase at a predetermined position of the electric component, based on the coincidence analysis voltage detected by said coincidence analysis voltage detecting unit,
wherein said phase voltage detecting unit detects the phase data indicating a phase of the jitter, based on a voltage of the signal at the phase detected by said phase voltage detecting unit and the voltage fluctuating amount.

11. An electron beam tester of claim 10, wherein said phase data detecting unit detects the phase data indicating a phase of the jitter, based on the waveform obtained by adding to voltages of the signal at a plurality of phases detected by said phase voltage detecting unit the voltage fluctuating amount at said phase.

12. An electron beam tester of claim 9, wherein said phase data detecting unit detects the phase data indicating a phase of the jitter, based on reference voltage change data which represent a relationship between a phase and a voltage fluctuation of a jitter-free reference signal, and the voltage fluctuating amount.

13. An electron beam tester of claim 1, wherein said voltage fluctuating data detecting unit detects the voltage fluctuating data by subtracting the first variation data from the second variation data.

14. A recoding medium storing an executable program in an electron beam tester comprising a drive circuit for supplying a signal to an electric component, an electron gun for causing to emanate a secondary electron from the electric component by irradiating an electron beam to a predetermined position of the electric component, and a detector for detecting an amount of the secondary electron emanated from the electric component and outputting a signal representing the amount of the secondary electron, the signal comprising a first phase including a substantially constant voltage and a second phase which follows the first phase and includes a non-constant voltage, the program comprising:
a first program calculating a signal outputted by a detector and generating a first distributed value indicating fluctuation of a voltage of the outputted signal, said first program value indicating fluctuation of a voltage of the outputted signal, the first program computing the first distributed value at a particular data of signal in the first phase;
a second program calculating the outputted signal and the first distributed value calculated by the first program and generating a second distributed value indicating fluctuation of a voltage of signal outputted by the detector, the second program generating a third distributed value by subtracting the first distributed value from the second distributed value, the second program calculating the second distributed value at a particular data of the outputted signal in the second phase; and
a third program calculating the third distributed value and generating a voltage with a phase data corresponding to the third distributed value.

15. A method of detecting data on a signal at a predetermined position of an electric component when testing the electric components, the signal data detecting method comprising:

causing to emanate a secondary electron from the electric component by irradiating an electron beam to the predetermined position of the electric component;

measuring an amount of the secondary electron;

calculating a signal representing the measured amount of the secondary electron, said generated signal comprising a first phase including a substantially constant voltage and a second phase which follows the first phase and includes a non-constant voltage;

generating a first distributed value indicating fluctuation of a voltage of the calculated signal in the first phase;

calculating out a second distributed value indicating fluctuation of a voltage of the calculated signal in the second phase;

generating a third distributed value calculated by subtracting the first distributed value from the second distributed value; and generating a voltage with a phase data which corresponds to the third distributed value.

* * * * *